United States Patent
Patterson

(10) Patent No.: US 9,585,738 B2
(45) Date of Patent: Mar. 7, 2017

(54) THREE BRUSH ELECTRONIC TOOTH BRUSH WITH SPLASH GUARD

(71) Applicant: Roosevelt Patterson, Fortson, GA (US)

(72) Inventor: Roosevelt Patterson, Fortson, GA (US)

(73) Assignee: Roosevelt Patterson, DDS, Fortson, GA (US)

( * ) Notice: Subject to any disclaimer, the term of this patent is extended or adjusted under 35 U.S.C. 154(b) by 0 days.

(21) Appl. No.: 14/684,202

(22) Filed: Apr. 10, 2015

(65) Prior Publication Data

US 2016/0296311 A1  Oct. 13, 2016

(51) Int. Cl.
*A61C 17/26* (2006.01)
*A61C 17/34* (2006.01)

(52) U.S. Cl.
CPC ............ *A61C 17/26* (2013.01); *A61C 17/349* (2013.01)

(58) Field of Classification Search
CPC .............................. A61C 17/26; A61C 17/349
See application file for complete search history.

(56) References Cited

U.S. PATENT DOCUMENTS

| 2,628,377 | A | * | 2/1953 | Cockriel | A61C 17/228 |
| | | | | | 15/167.1 |
| 2,758,326 | A | * | 8/1956 | Keely | A61C 17/26 |
| | | | | | 15/23 |
| 2006/0021166 | A1 | * | 2/2006 | Hills | A46B 13/005 |
| | | | | | 15/23 |

FOREIGN PATENT DOCUMENTS

JP  2011177397 A  *  9/2011

* cited by examiner

*Primary Examiner* — Shay Karls

(57) ABSTRACT

Implementations of a tooth brush are provided. In some implementations, the tooth brush comprises a handle and a head attached to the handle where the head comprises three gears and three brushes attached to the three gears respectively. In some implementations, the tooth brush is configured such that one brush makes contact with the occlusal surfaces of a plurality of teeth and the remaining brushes make contact with the buccal side and lingual side of the plurality of teeth. In some implementations, the tooth brush further comprises a splash guard. In some implementations, the tooth brush further includes a suction tube to remove debris from the mouth. Methods of using the tooth brush also are provided.

14 Claims, 1 Drawing Sheet

THREE BRUSH ELECTRONIC TOOTH BRUSH WITH SPLASH GUARD

TECHNICAL FIELD

This disclosure relates to implementations of tooth brushes.

BACKGROUND

Cleaning the teeth of persons unable to brush their own teeth (e.g., hospital or nursing homing patients) and animals can be messy and difficult. With existing tooth brushes, the tops and sides of the teeth have to be cleaned separately. There do not exist tooth brushes for cleaning the top and sides of teeth simultaneously.

DETAILED DESCRIPTION

Implementations of a tooth brush are provided. In some implementations, the tooth brush comprises a handle and a head attached to the handle where the head comprises three gears and three brushes attached to the three gears respectively. In some implementations, the tooth brush is configured such that one brush makes contact with the occlusal surfaces of a plurality of teeth and the remaining brushes make contact with the buccal side and lingual side of the plurality of teeth. In some implementations, the tooth brush further comprises a splash guard. In some implementations, the tooth brush further includes a suction tube to remove debris from the mouth. Methods of using the tooth brush also are provided.

Figure 1:
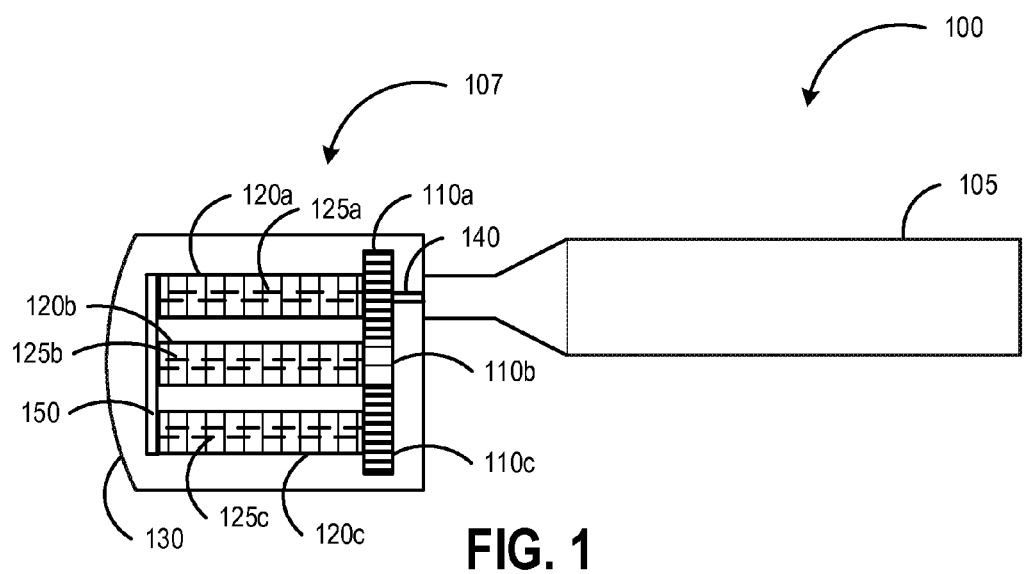
FIG. 1 illustrates an implementation of an example tooth brush according to the principles of the present disclosure.

FIG. 1 illustrates an implementation of an example tooth brush 100 according to the principles of the present disclosure. In some implementations, a tooth brush 100 comprising a handle 105 and a head 107 attached to the handle 105 where the head 107 comprises three gears 110a, 110b, and 110c (collectively gears 110) and three brushes 120a, 120b, and 120c (collectively brushes 120) attached to the gears 110a, 110b, 110c, respectively. In some implementations, the tooth brush 100 further comprises a splash guard 130. In some implementations, the tooth brush 100 further includes a suction tube or an attachment for an external suction tube to remove debris from the mouth.

In some implementations, the three gears work in tandem. In some implementations the first gear 110a meshes with the second gear 110b and the second gear 110b meshes with the third gear 110c.

In some implementations, each brush comprises a shaft and bristles extending from the shaft in all direction thereby creating a circular brush. In this way, the brush may brush the teeth as the brush rotates and come into contact with a person's teeth. In some implementations, the first shaft 125a of the first brush 120a extends from the first gear 110a, the second shaft 125b of the second brush 120b extends from the second gear 110b, and the third shaft 125c of the third brush 120c extends from the third gear 110c.

In some implementations, each brush comprises a cylindrical shape body with bristles extending therefrom in all directions and a shaft extending therethrough thereby creating a circular brush. In this way, the brush may brush the teeth as the brush rotates and come into contact with a person's teeth.

In some implementations, the brushes are replaceable. In some implementations, the shafts of the brushes are removable from the gears.

In some implementations, the brushes may be secured on the distal end by a piece of material 150 having openings for receiving the shafts of the brushes.

In some implementations, one or more of the brushes may be tapered to contour to the teeth. For example, in some implementations, the first and third brushes may be tapered. In some implementations, all of the brushes may be tapered.

In some implementations, the first gear 110a may be attached to fourth shaft that is rotated by a motor (not shown) that may be housed in the handle 105. In some implementations, the motor is battery powered. In some implementations, the motor may rotate in two directions. The rotation of the shaft 140 causes the gears 110 and therefore the brushes 120 to rotate.

In some implementations, the first brush 120a and the third brush 120c rotate in a counter-clockwise position while the second brush 120b rotates in a clockwise position. In some implementations, the first brush 120a and the third brush 120c rotate in a clockwise position while the second brush 120b rotates in a counter-clockwise position. In some implementations, the rotation of the gears and brushes may be 360 degrees.

In some implementations, the second gear 110b (and therefore the second brush 120b) may be elevated from the first 110a (brush 120a) and third 110c gear (brush 120c).

In some implementations, the gears 110 and brushes 120 are configured such that the first brush 120 and third brush 120c are spaced sufficiently apart to insert a tooth 210 (see FIG. 2) in between the first brush 120 and third brush 120c.

Figure 2:
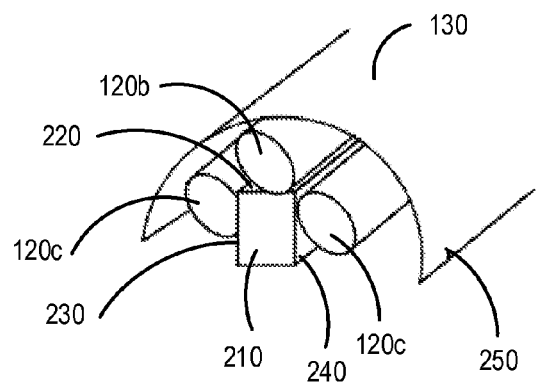
FIG. 2 illustrates an implementation of an example method of using the tooth brush.

As shown in FIG. 2, the splash guard 130 may be configured to cover the top and sides of the brushes 120. In this way, as the tooth brush 100 is used, splatter may be contained.

In some implementations, an attachment device may be provided to attach an external suction tub to the tooth brush 100. In some implementations, the attachment device may be located on the outside surface of the splash guard 130. In some implementations, the attachment device may be located on the inside surface of the splash guard 130. In some implementations, the attachment device may be in any suitable location on the splash guard 130 or tooth brush 100. In some implementations, the attachment device may be a hook 250 to hold a portion of the suction tube. In some implementations, the attachment device may be any device to hold a portion of the suction tube.

Referring to FIG. 2, to use the tooth brush 100 to brush a person's or animal's teeth, first, the toothbrush is positioned such that the second brush 120b rests on the occlusal surfaces 220 of a plurality of teeth 210. In some implementations (depending on the direction of the brush), the first brush 120a may rest on the lingual side 240 of the teeth 210 as the brush 120a rotates toward the occlusal surfaces of the teeth 210 and the third brush 120c may rest on the buccal side 230 of the teeth 210 as the brush 120c rotates toward the occlusal surfaces of the teeth 210.

In some implementations (depending on the direction of the brush), the first brush 120a may rest on the buccal side of the teeth as the brush 120a rotates toward the occlusal surfaces of the teeth, and the third brush 120c may rest on the lingual side of the teeth as the brush 120c rotates toward the occlusal surfaces of the teeth 210.

In this way, a plurality of teeth and a plurality of surfaces may be brushed simultaneously.

In some implementation, as the tooth brush is positioned in different quadrants of the mouth, the direction of the motor may have to be changed so that the first and third brushes rotate toward the occlusal surfaces of the teeth.

Reference throughout this specification to "an embodiment" or "implementation" or words of similar import means that a particular described feature, structure, or characteristic is included in at least one embodiment of the present invention. Thus, the phrase "in some implementations" or a phrase of similar import in various places throughout this specification does not necessarily refer to the same embodiment.

Many modifications and other embodiments of the inventions set forth herein will come to mind to one skilled in the art to which these inventions pertain having the benefit of the teachings presented in the foregoing descriptions and the associated drawings.

The described features, structures, or characteristics may be combined in any suitable manner in one or more embodiments. In the above description, numerous specific details are provided for a thorough understanding of embodiments of the invention. One skilled in the relevant art will recognize, however, that embodiments of the invention can be practiced without one or more of the specific details, or with other methods, components, materials, etc. In other instances, well-known structures, materials, or operations may not be shown or described in detail.

While operations are depicted in the drawings in a particular order, this should not be understood as requiring that such operations be performed in the particular order shown or in sequential order, or that all illustrated operations be performed, to achieve desirable results.

The invention claimed is:

1. A tooth brush comprising:
 a handle wherein the handle is elongated having a distal end and a proximal end; and
 a head attached to the distal end of the handle wherein the head comprises:
 a first gear, a second gear, and a third gear wherein the first gear meshes with the second gear and the second gear meshes with the third gear and;
 a first brush, a second brush, and a third brush extending from the first gear, the second gear, and the third gear, respectively, wherein the second brush is elevated above the first brush and third brush and
 wherein the gears and brushes are configured such that the first brush and third brush are spaced sufficiently apart to insert a plurality of teeth between the first brush and third brush and wherein the gears are configured such that the first brush and the third brush rotate in a first direction and the second brush rotates in a second direction opposite the first direction when the first gear is attached to a motor.

2. The tooth brush of claim 1 wherein each brush comprises a shaft and bristles extending from the shaft in all direction thereby creating a circular brush wherein a first shaft of the first brush extends from the first gear, a second shaft of the second brush extends from the second gear, and a third shaft of the third brush extends from the third gear.

3. The tooth brush of claim 1 wherein each brush comprises an elongated cylindrical shape body with bristles extending therefrom in all directions and a shaft extending therethrough thereby creating a circular brush wherein a first shaft of the first brush extends from the first gear, a second shaft of the second brush extends from the second gear, and a third shaft of the third brush extends from the third gear.

4. The tooth brush of claim 1 wherein the brushes are removably attached to the gears.

5. The tooth brush of claim 1 wherein each brush comprises a shaft wherein a first shaft of the first brush extends from the first gear, a second shaft of the second brush extends from the second gear, and a third shaft of the third brush extends from the third gear, the tooth brush further comprising a piece of the material having a first opening, a second opening, and a third opening wherein the distal end of the first shaft is housed in the first opening, the distal end of the second shaft is housed in the second opening, and the distal end of third shaft is housed in the third opening.

6. The tooth brush of claim 1 wherein one or more of the brushes are tapered.

7. The tooth brush of claim 1 wherein the first gear is attached to a fourth shaft extending from the first gear in the head into the handle wherein the fourth shaft on the proximal end is attached to a motor in the handle and the motor is configured to rotate in two directions.

8. The tooth brush of claim 1 further comprising a splash guard that extends above the brushes and along the sides of the first brush and third brush.

9. The tooth brush of claim 1 further comprising a suction tube.

10. The tooth brush of claim 1 further comprising an attachment device configured to hold a suction tube.

11. The tooth brush of claim 10 further comprising a splash guard that extends above the brushes and along the sides of the first brush and third brush wherein the attachment device is located on the splash guard.

12. The tooth brush of claim 10 wherein the attachment device is a hook.

13. A method of using the tooth brush of claim 1, comprising:
 contacting the occlusal surfaces of a plurality of teeth with the second brush;
 contacting the lingual side of the plurality of teeth with either the first or third brush; and
 contacting the buccal side of the plurality of teeth with the other of the first or third brush.

14. A tooth brush comprising:
 a handle wherein the handle is elongated having a distal end and a proximal end;
 a head attached to the distal end of the handle wherein the head comprises a first gear, a second gear, and a third gear wherein the first gear meshes with the second gear and the second gear meshes with the third gear and a first brush, a second brush, and a third brush extending from the first gear, the second gear, and the third gear, respectively, wherein the second brush is elevated above the first brush and third brush;
 a suction tube; and
 a splash guard that extends above the brushes and along the sides of the first brush and third brush,
 wherein the gears and brushes are configured such that the first brush and third brush are spaced sufficiently apart to insert a plurality of teeth between the first brush and third brush;
 wherein the first gear is attached to a fourth shaft extending from the first gear in the head into the handle wherein the fourth shaft on the proximal end is attached to a motor in the handle and the motor is configured to rotate in two directions;
 wherein the gears are configured such that the first brush and the third brush rotate in a first direction and the second brush rotates in a second direction opposite the first direction when the first gear is attached to a motor.

\* \* \* \* \*